(12) United States Patent
Berno

(10) Patent No.: US 7,058,657 B1
(45) Date of Patent: Jun. 6, 2006

(54) ARCHITECTURE FOR DEVELOPING AND REUSING ANALYTIC AND VISUALIZATION COMPONENTS AND METHODS OF USE THEREOF

(75) Inventor: Anthony J. Berno, San Jose, CA (US)

(73) Assignee: Perlegen Sciences, Inc., Mountain View, CA (US)

( * ) Notice: Subject to any disclaimer, the term of this patent is extended or adjusted under 35 U.S.C. 154(b) by 520 days.

(21) Appl. No.: 10/338,769

(22) Filed: Jan. 7, 2003

(51) Int. Cl.
*G06F 17/30* (2006.01)

(52) U.S. Cl. .................. 707/103 R; 707/100; 707/101; 707/102; 707/104.1

(58) Field of Classification Search ................ 707/100, 707/101, 102, 103 R, 104.1
See application file for complete search history.

(56) References Cited

U.S. PATENT DOCUMENTS

| | | | | |
|---|---|---|---|---|
| 5,339,392 A | * | 8/1994 | Risberg et al. | 715/762 |
| 5,764,221 A | * | 6/1998 | Willard | 345/173 |
| 5,778,350 A | * | 7/1998 | Adams et al. | 707/1 |
| 5,786,815 A | * | 7/1998 | Ford | 715/744 |
| 5,832,496 A | * | 11/1998 | Anand et al. | 707/102 |
| 6,229,694 B1 | * | 5/2001 | Kono | 361/683 |
| 6,266,716 B1 | * | 7/2001 | Wilson et al. | 710/33 |
| 6,272,673 B1 | * | 8/2001 | Dale et al. | 717/100 |
| 6,549,890 B1 | * | 4/2003 | Mundell et al. | 705/10 |
| 6,704,804 B1 | * | 3/2004 | Wilson et al. | 719/315 |
| 6,751,653 B1 | * | 6/2004 | Austin | 709/217 |
| 6,778,987 B1 | * | 8/2004 | Wynblatt et al. | 707/10 |
| 6,877,150 B1 | * | 4/2005 | Miller et al. | 716/18 |
| 6,920,608 B1 | * | 7/2005 | Davis | 715/503 |
| 6,952,688 B1 | * | 10/2005 | Goldman et al. | 706/45 |

\* cited by examiner

*Primary Examiner*—Frantz Coby
(74) *Attorney, Agent, or Firm*—Beyer Weaver & Thomas, LLP

(57) ABSTRACT

An interactive and dynamic data analysis tool that helps interactive analysis in real time on medium size datasets having complex structure is described. In one aspect, the data analysis tool is capable of being configured to act as a data producer tool arranged to provide a data source. The data analysis tool can also be configured as a data consumer tool capable of receiving and processing a particular data source. The data source tool and the data consumer tool are connected together to form a framework that takes the form of a data mapping context that mediates the data provided by the data source and a particular data role.

19 Claims, 17 Drawing Sheets

ARCHITECTURE FOR DEVELOPING AND REUSING ANALYTIC AND VISUALIZATION COMPONENTS AND METHODS OF USE THEREOF

BACKGROUND OF THE INVENTION

The invention relates to interactive data analysis. More particularly, a software architecture and associated framework that facilitates interactive analysis in real time is described.

Computer-based research tools are increasingly being used for a variety of purposes related to genetic research. These computer-based tools include both hardware and software that perform high-speed algorithms and data analysis tools that are used to analyze data stored in a database. One such analysis that is performed is referred to as genetic association studies. The objective of a typical association study is to discover an association (if any) between an allele and disease phenotype typically requiring interactive data analysis on databases having approximately 100,000 rows of data.

Although a large number of data analysis products (such as Microsoft Access™) work well with highly structured data, they do not provide satisfying visualization capabilities (such as providing a user friendly user interface or other data display functionalities) that would enhance the associated process. In some cases, however, data analysis products (such as Autodesk™) that do offer visualization on large data sets, rely on a single flat table type of data base. In other cases, the available data analysis tools are not particularly interactive thereby inhibiting an easy and user friendly data analysis experience.

For example, a typical association study requires various regression analyses to be performed iteratively that are clearly difficult to perform on any large data set without the data analysis product having effective interactive visualization capabilities. Using conventional data analysis tools in order to perform an association study, the analyst is required to move from one data tool to another resulting in an increase in potential error, inefficient use of time and computing resources, and otherwise reducing overall analytical efficiencies.

Therefore, improved data analysis tool is desired.

SUMMARY OF THE INVENTION

According to the present invention, an efficient and dynamic data analysis tool that helps interactive analysis in real time on medium size datasets having complex structure is described.

In one embodiment, a method of configuring an interactive data analysis application arranged to perform real time data analysis of selected data from a complex data base in an object oriented computing environment is described. A configurable data tool object is instantiated where the data tool object is configurable as any type of appropriate data analysis application components. The data tool object is configured as a data producer for providing access to the selected data and as a data consumer for providing the data analysis of the selected data. A mapping context that associates the data producer to the data consumer is instantiated that maps the data producer to the data consumer.

In another aspect of the invention, the data tool can be configured as a data producer/consumer object that acts as both a data consumer and data producer.

In yet another aspect of the invention, a particular end user can prepackage useful functionality by creating a workspace file for another end user and dynamically loading separate files into that workspace. In this way, a custom application can be made available to another end user without resource intensive compilation of the application.

In yet another embodiment, computer program product for providing an interactive data analysis application in an object oriented computing environment is described. The computer program product includes computer code for computer code for instantiating a configurable data tool object wherein the data tool object is configurable as any of a number and type of data analysis application components computer code for configuring the data tool object as a data producer for providing access to the selected data, computer code for configuring the data tool object as a data consumer for providing the data analysis of the selected data, computer code for instantiating a mapping context that associates the data producer to the data consumer, and computer code for mapping the data producer to the data consumer by way of the mapping context.

In still another embodiment of the invention, in an object oriented computing environment, an interactive data analysis application arranged to perform real time data analysis of selected data from a complex data base is described. The application includes a configurable data tool object wherein the data tool object is configurable as any of a number and type of data analysis application components wherein the data tool object is configured as a data producer for providing access to the selected data and as a data consumer for providing the data analysis of the selected data. The application also includes a mapping context that associates the data producer to the data consumer form the interactive data analysis application

BRIEF DESCRIPTION OF THE DRAWINGS

The invention will be better understood by reference to the following description taken in conjunction with the accompanying drawings.

DETAILED DESCRIPTION OF SELECTED EMBODIMENTS

Figure 1:
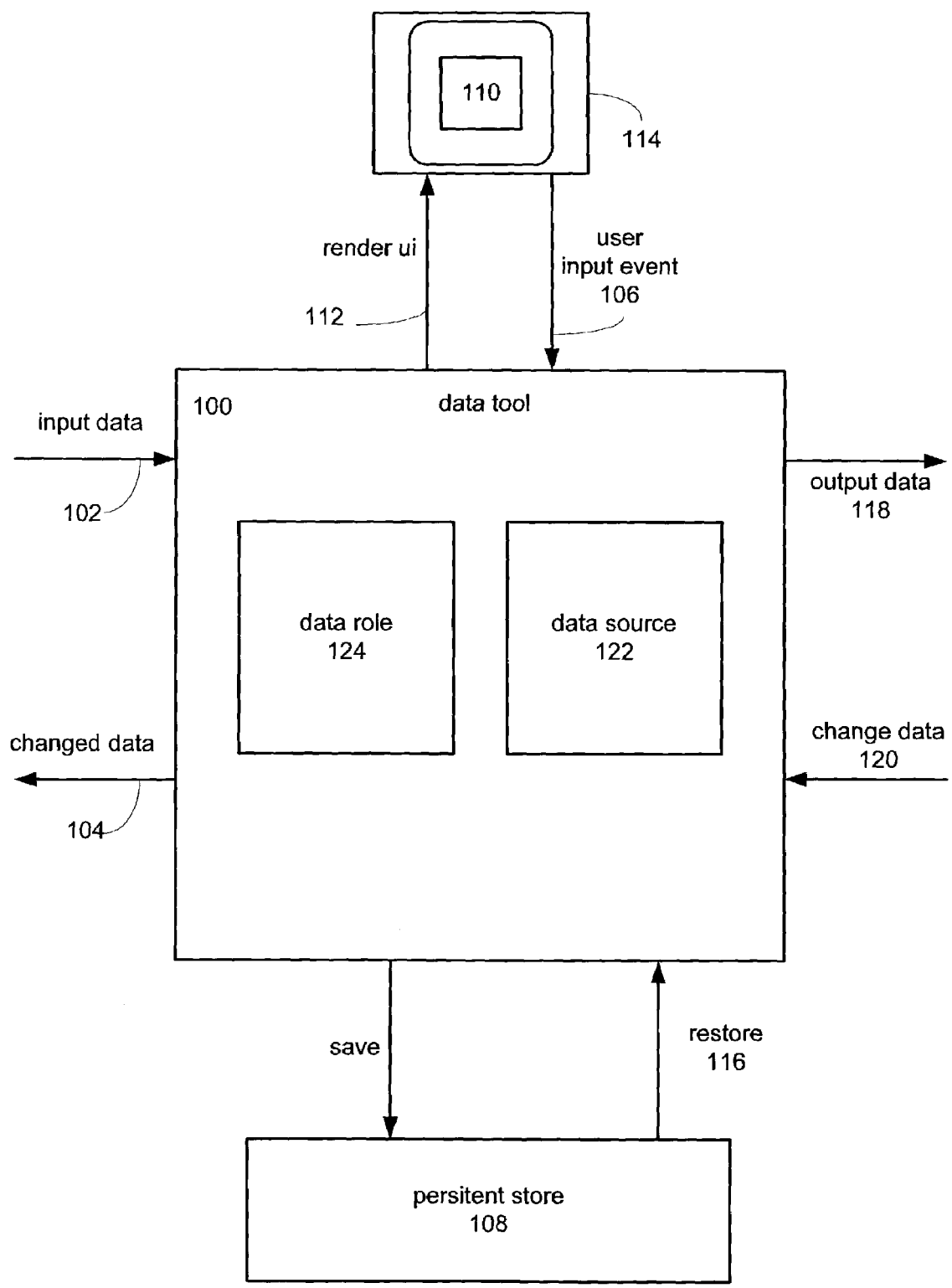
FIG. 1 shows an exemplary configurable data tool in accordance with an embodiment of the invention.

Reference will now be made in detail to a particular embodiment of the invention an example of which is illustrated in the accompanying drawings. While the invention will be described in conjunction with the particular embodiment, it will be understood that it is not intended to limit the invention to the described embodiment. To the contrary, it is intended to cover alternatives, modifications, and equivalents as may be included within the spirit and scope of the invention as defined by the appended claims.

As used herein, the term "distributed object" or "object" refers to an encapsulated package of code that can be manipulated by operations through a defined interface that is associated with the object. Thus, distributed objects will be seen by those skilled in the art as including the basic properties that define traditional programming objects. However, distributed objects differ from traditional programming objects by the inclusion of two important features. First, distributed objects are multilingual. The interfaces of distributed objects are defined using an interface definition language that can be mapped to a variety of different programming languages. One such interface definition language is OMG's IDL. Second, distributed objects are location-independent, i.e., distributed objects can be located anywhere in a network. This contrasts sharply with traditional programming objects which typically exist in the same address space as the client. Distributed objects can be object clients or object servers, depending upon whether they are sending requests to other objects or replying to requests from other objects. Requests and replies are made through an Object Request Broker (ORB) that is aware of the locations and status of the objects.

A "distributed object system" or "distributed object operating environment" refers to a system comprising distributed objects that communicate through an ORB. An "object reference" or "objref" is a value that contains a pointer or some other type of indirection to an object. The creation and definition of object references will be familiar to those skilled in the art. A "client" as defined herein refers to an entity that sends a request to second object. In this model, the second object is referred to as a "server object" or a "target object". Thus, clients invoke operations, or implementations, from servers. In a distributed object environment, clients need not have knowledge of the implementation programming language, nor does the implementation have to have knowledge of the client's programming language due to the requirement of multilingual character of such objects. Clients and servers in distributed object environments need only communicate in terms of the interface definition language. As noted above, the request by the client to the server, and the server's reply to the client, is handled by the ORB. It should be pointed out that the client and server can exist within the same process, on the same host computer, or on two different host computers.

An "object interface" is a specification of the operations, attributes, and exceptions that an object provides. Preferably, object interfaces for distributed objects are written using an IDL. As noted above, objects perform services through their interfaces. The use of interfaces therefore relieves the need of clients to be aware of the programming languages used to define the methods and data of the objects in the service.

Accordingly, in an object oriented computing environment, an efficient and dynamic data analysis tool that helps interactive analysis in real time on medium size datasets having complex structure is described. In one aspect, the data analysis tool is capable of being configured to act as a data producer tool arranged to provide a data source. In a particular embodiment, the data source is formed of a data table having a number of data columns. It should be noted, however, that a data producer can, in fact, be associated with any number of data sources each having an associated data table. On the other hand, the data analysis tool can be configured as a data consumer tool capable of receiving and processing a particular data source. In the described embodiment, the data source tool and the data consumer tool are connected together to form a framework using a data mapping context to form the framework capable of providing a dynamic data analysis tool that helps interactive analysis in real time.

An aspect of the invention provides for configuring the data analysis tool to act as both a data source tool and a data role tool. In this way, a tool network can be formed providing a basis for creating a custom end user application specifically tailored for a particular need. For example, a particular end user can prepackage useful functionality by creating a workspace file for another end user and dynamically loading separate files into that workspace. In this way, a custom application can be made available to another end user without resource intensive compilation of the application.

The invention will now be described in terms of an exemplary framework having a data source tool and a data consumer tool. It should be noted, however, that any number of data source tools and data consumer tools can be included in the framework based upon the requirements of a particular data analysis program.

Accordingly, FIG. 1 shows an exemplary configurable data tool 100 in accordance with an embodiment of the invention. In general, the data tool 100 requires data from an external data source in the form of input data source 102. In some cases, the data tool 100 can dynamically modify selected portions of the source data using a change data request 104 provided by, for example, a user input event 106 or an internally created change data request depending, of course, on the particular change required. In some cases, the change request 104 results in a data tool state change that can be saved in a persistent store 108 (that can any number of forms, such as SDRAM) coupled to the data tool 100. It should be noted that in most cases, the user input event 106 is generated by a user interface 110 configured and rendered by the data tool 100 using a render user interface command 112. It is contemplated, that in addition to rendering an interactive user interface, the data tool 100 also provides real time feedback and display of the input source data 102 on a display unit 114 as well as changes in the source data based upon the change data request 104. In this way, a particular user can readily observe the data that is being analyzed as well as any changes (either proposed or effected) to the data.

At the discretion of a user (or based upon particular analysis requirements), a current state of the data tool 100 can be stored in the persistent store 108 and marked as a previous, or stored, state. In this way, a mechanism for replacing (i.e., restoring) a subsequent current state with the stored state is provided by way of a restore event 116. The data tool 100 also provides output data 118 based upon the operation of the data tool 100 on the source data 102 in conjunction with any user input events, source data change requests, etc. In some cases, the output data 118 can be changed using an output data change request 120.120.

In the described embodiment, the data tool 100 includes a data source module 122 and a data consumer module 124 that enables the data tool 100 to be configured as any of a number of data analysis components that include a data producer, a data consumer, or a data producer/consumer. When configured as a data producer, the data tool 100 accesses selected data from an associated data base. The selected data, in turn, is made accessible to an associated data consumer(s) (and/or a data producer/consumer) configured to process the selected data based upon a specific (typically user supplied) data analysis protocol. Such protocols may include any number of graphical analysis protocols (i.e., scatter plot, for example) and/or statistical analysis protocols (such as multidimensional representations, principal component analysis, frequency based representations or regression analyses) as well as any number and kind of data transformation protocols (such as, for example, eigenvalue calculations). For example, in the case where the data consumer is configured to provide a scatter plot of selected data provided by an associated data producer, the data consumer renders a scatter plot based upon specific user provided instructions (such as axis labeling, and such). It should be noted that in those cases where the data tool 100 is configured as a data consumer/producer, the data consumer portion processes data as would any data consumer. The processed data is, in turn, made accessible by the data producer portion to another component(s) that uses the processed data as source data to be processed according to that particular component's data processing protocol. In this way, a data analysis application can be configured as needed for a particular data analysis application.

In some cases, the data tool 100 renders a virtual window providing a user the ability to view (and in some cases manipulate) in real time a current state of the data tool 100 (such as current data values) by using, for example, a display unit and an associated user interface. In this way, the data tool 100 provides a mechanism for real time interactive data analysis at any point in a data analysis application thereby helping to improve a user's ability to perform complex data analysis on large data sets.

Figure 2:
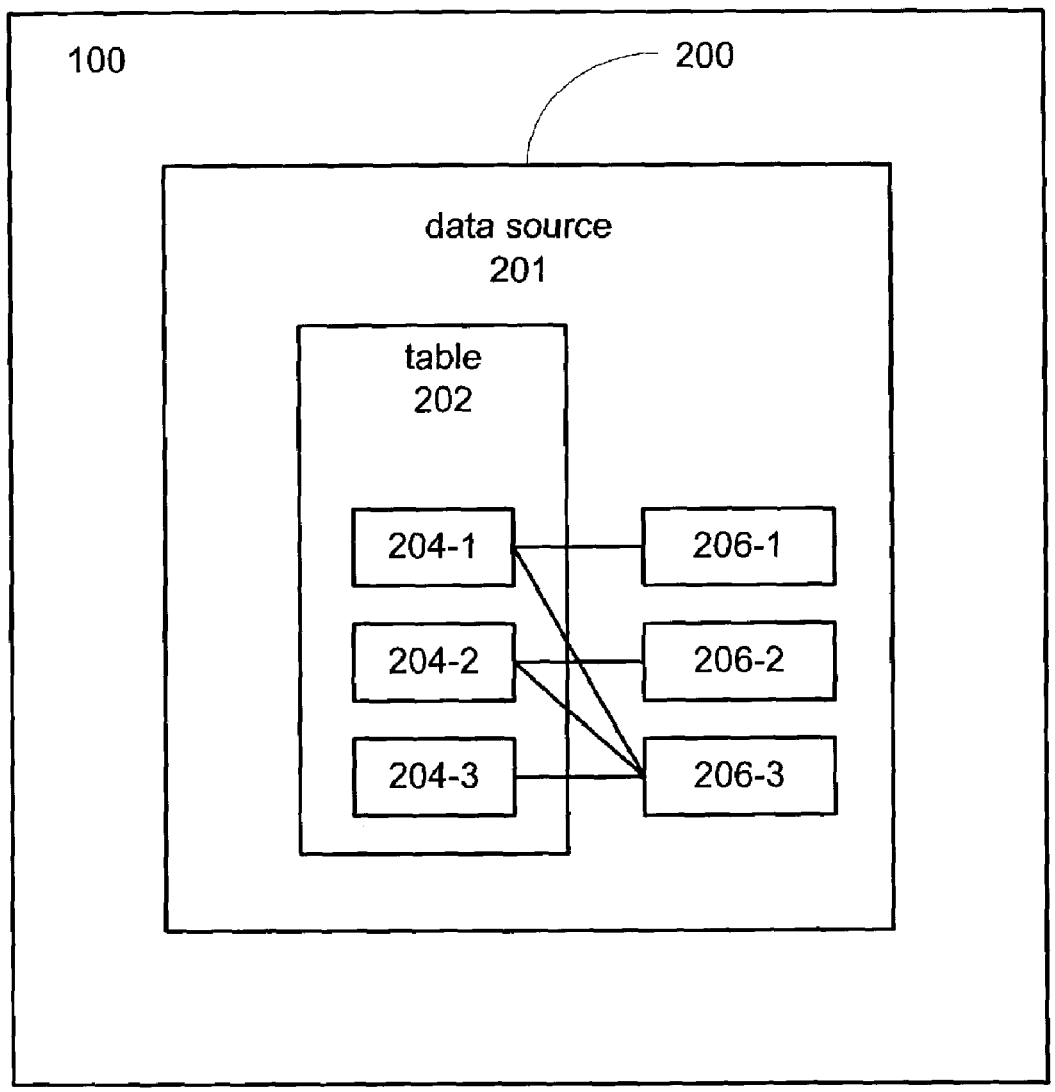
FIG. 2 shows a particular implementation of a producer tool in accordance with an embodiment of the invention.

FIG. 2 is an example of the data tool 100 configured as a data producer 200 suitable for providing access to selected data from any number and type of data bases to an associated data consumer. In the illustrated embodiment, the data producer 200 includes a data source(s) 201 having a data table 202 that includes a set of flat data tables 204 formed of rows of column-wise data 204. A column source 206 categorizes and describes an associated data column to which it is linked by an identifying name associated therewith. For example, as shown in FIG. 2, the data table 202 includes data arranged as data columns 204-1 through 204-3 and a number of column sources 206-1 through 206-3. As configured, the column source 206-1 is associated with the column data 204-1 whereas the column data 204-2 is associated with both the column source 206-2 and 206-3. In this way, the data represented by the columns 204-1 and 204-2 are categorized and described by the associated column sources 206-1 through 206-3. It should be noted that although most data producers are created having a fixed number of columns, it is contemplated that when desired, the number of columns can be dynamically changed. This may be necessary when the number of columns of data required is not known when the data producer is instantiated.

Just such a situation is encountered during what is referred to as a pivot transformation whereby a flat table is transformed into a two dimensional array. During a pivot operation, the columns of output depend on the data from the input so that if a particular data tool is contemplated to provide a pivot type transformation operation, then the columns can't be identified at the creation of the tool since the input data is not known at that point. In this situation, the column sources are dynamically mapped to the appropriate column. In this way, column sources provide a mechanism for classifying sets of columns when the columns are undetermined until input data is available.

Figure 3:
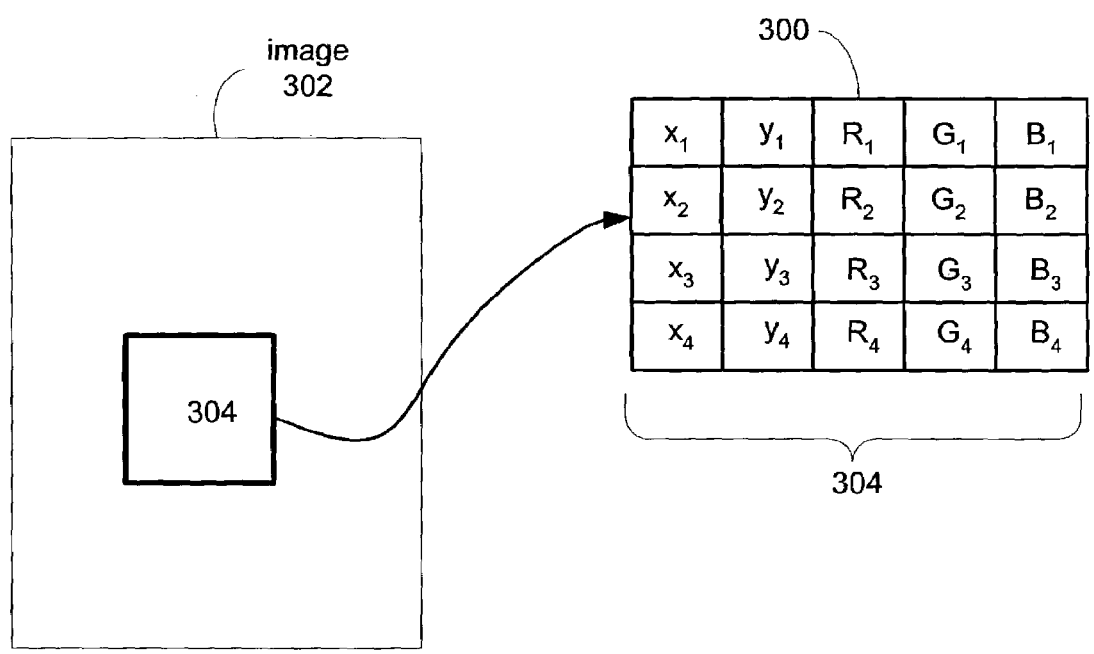
FIG. 3 illustrates a data table associated with an image in accordance with an embodiment of the invention.

In order to more clearly describe the data producer 200, FIG. 3 shows a data table 300 associated with a digital image 302 (which represents the source data base in this example). At this point in the discussion, it would be useful to describe the digital image 302 in terms of a source of data suitable for being accessed by the data producer 200. Accordingly, a digital image is formed of a number of "picture elements" (referred to in the vernacular as pixels) that constitute the smallest unit of display. In this way, a resolution of an image is the total number of pixels available for display that are typically measured as rows of pixels by columns of pixels. In most display environments, each pixel is assigned a particular color value that depends upon the particular color space is being used. For example, in most display technologies that use what is referred to as an RGB color space, a pixel is assigned a Red (R) component, a Green (G) component, and a Blue(B) component which determines the color (or shade thereof) ultimately displayed. Therefore, any digital image can be viewed as a collection of Cartesian coordinates (i.e., x, y) each of which has an associated pixel, which in turn has an associated RGB color value (i.e., the various RGB color components) for a total of 5 values for each pixel in the display.

Accordingly, since the data table 300 is associated with the digital image 302, the data table 300 is formed in such as way as to provide a construct whereby an (x,y) co-ordinate of a particular pixel (i.e., "x", "y") is associated with that pixel's corresponding color value (which in this case is based on the Red, Green, Blue (RGB) color space). In this way, each pixel of the image 302 is represented in the data table 300 has an associated number of columns (which in this case is "x, y, R, G, B") arranged in a row wise manner that taken together provide the entire image data set for the image 302. Accordingly, the number of rows in the data table 300 are equal to the number of pixels (either in the entire image 302 or a selected subset 304 of the image data). It should be noted, however, that the table 300 is not necessarily arranged in the manner shown in FIG. 3 but can be arranged in any manner deemed appropriate for the situation at hand. Additionally, the table 300 can be a dynamic table in that the size and content of the table 300 can change whenever the underlying data source (which in this case is the image 302, or a subset 304) is changed.

Figure 4:
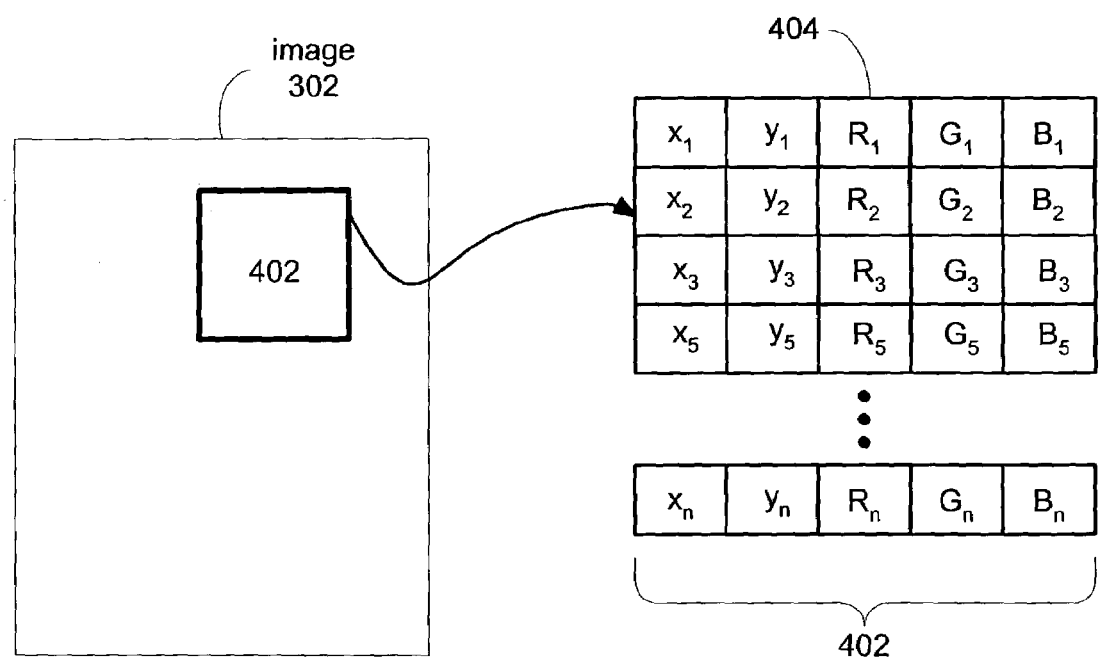
FIG. 4 shows the data table of FIG. 3 updated to reflect any changes in the source data.

Accordingly, when a user input event, for example, causes the source data to change from a current state to a next state (such as is the case when the selected portion of the image 302 is changed from the subset 304 to a subset 402 shown in FIG. 4), the data table 300 is updated to reflect any changes in the source data in the form of a data table 404. This updating can occur real time or, if desired, can occur at some subsequent time depending on the particular circumstances. In this way, the dynamic updating of the various data tables provides a mechanism whereby a user can select only that portion of a data base that is needed for a particular analysis and have that new subset of data be immediately displayed or otherwise processed interactively.

Figure 5:
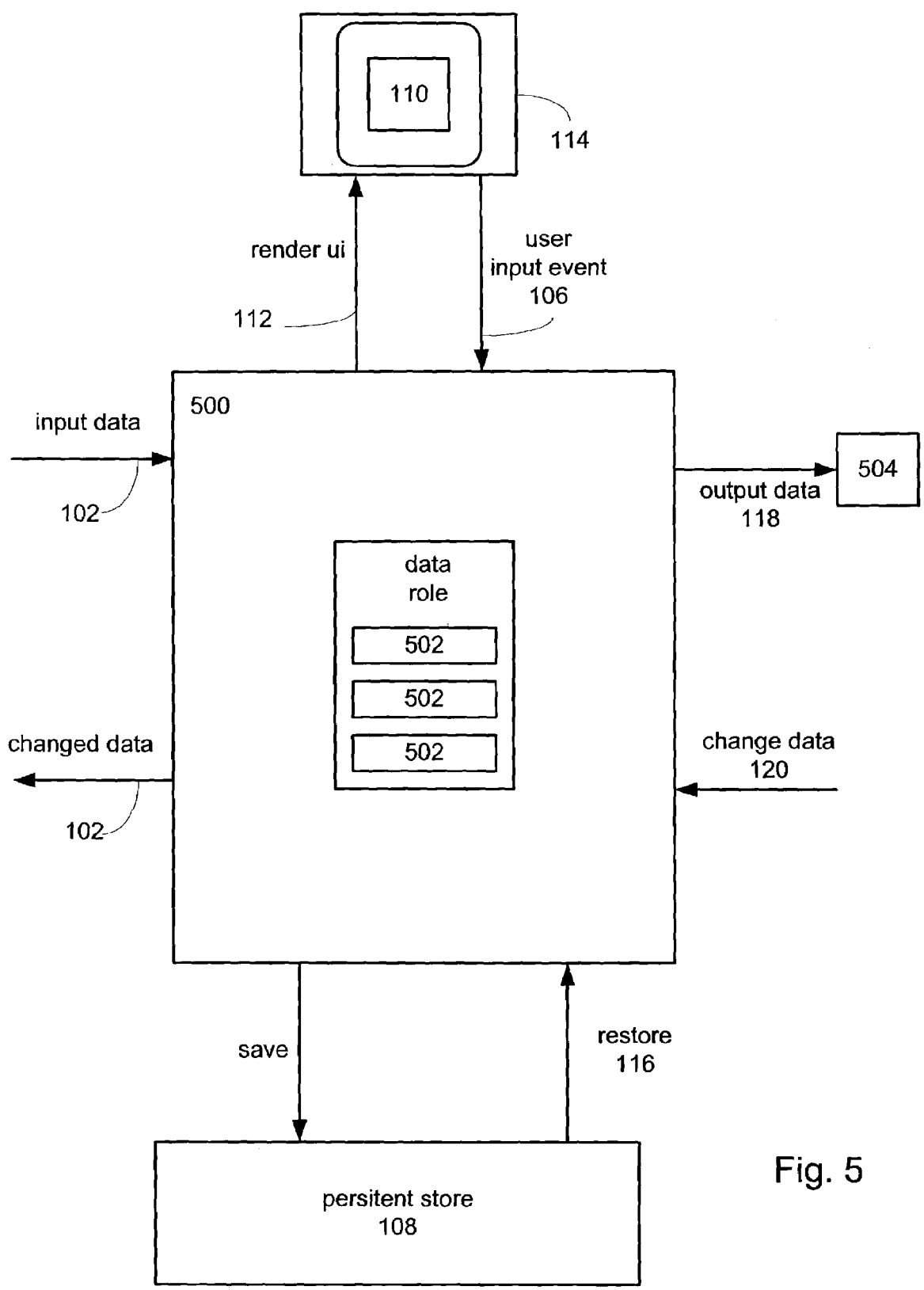
FIG. 5 shows the data tool of FIG. 1 configured to act as a data consumer in accordance with an embodiment of the invention.

In addition to being configured as a data producer, the data tool 100 can be configured to act as a data consumer 500 as shown in FIG. 5. Accordingly, the data consumer 500 includes a number of data roles 502 that define a particular data processing protocol in terms of the kind and type of data that it can process. For example, in keeping with the prior examples, when the data consumer 500 is configured as a grid tool 500, selected pixel co-ordinates and associated RGB color data is displayed in a grid-like manner having a header portion having a number of column headings (i.e., "x,y,R,G,B") and body portion that includes the data values structured in columns each being associated with one of the headings.

Figure 6:
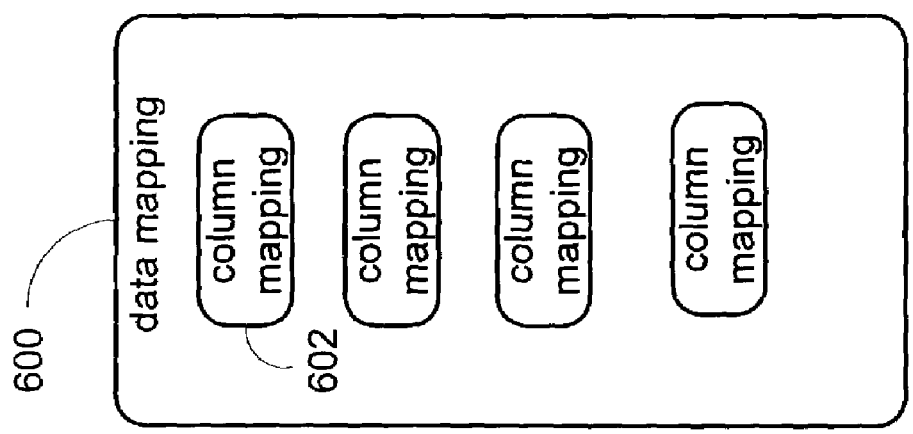
FIG. 6 shows an example of a data mapping context in accordance with an embodiment of the invention.

In order for the grid tool 500 to be able to access and properly process the correct source data, the grid tool 500 is mapped to the source tool 200 by way of a data mapping context 600 shown in FIG. 6. In the described embodiment, the mapping context 600 includes a number of column mappings 602 that are used to map a data column(s) in the data producer 200 to a data role(s) in the data consumer 500. In this way, a particular data role receives the appropriate kind and type of data from the data source since certain of the column sources 206 are mapped (statically or dynamically, if necessary) to only certain of the data roles 502.

Figure 7:
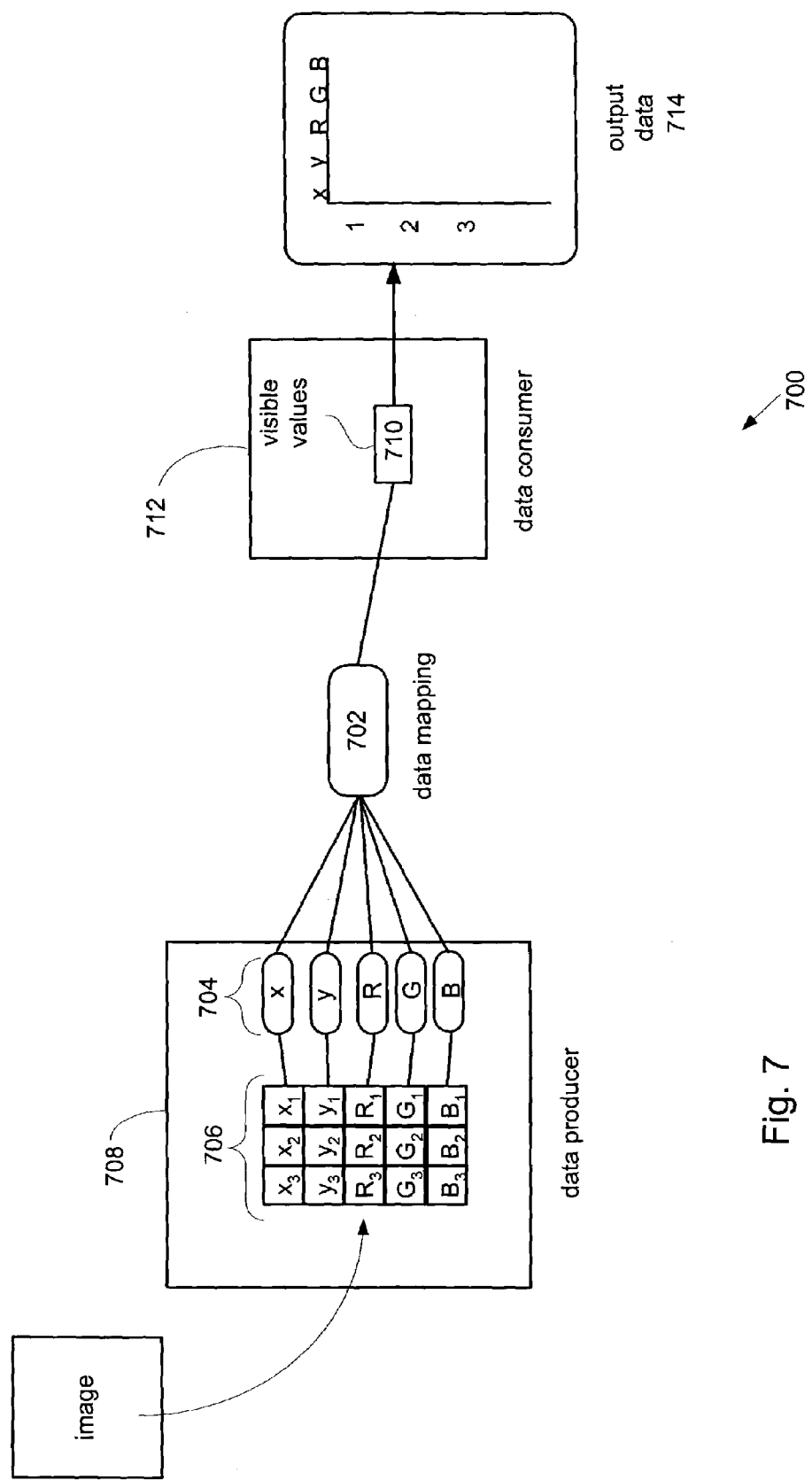
FIG. 7 illustrates an exemplary framework (application) in accordance with an embodiment of the invention.

For example, FIG. 7 shows a particular implementation of an image data display application 700 arranged to display pixel based image data in a grid format. In the described embodiment, the application 700 is configured by defining a mapping context 702 that links selected data columns 704 in an image data table 706 in an image tool 708 to a "visible values" data role 710 in a grid display tool 712. By visible values it is meant that selected pixel data (i.e., x,y co-ordinates and selected ones of the associated RGB color components) are displayed as output data 714 in a grid format rendered by the grid display tool 712 based upon a display protocol incorporated therein.

Therefore, when the application 700 is executing, the image tool 708 provides access of the image data table 706 to the grid display tool 712 as defined by the mapping context 702. The grid display tool 712, in turn, processes the accessed image data based upon the data processing protocol defined by the visible values data role 710. In this case, the processing protocol includes rendering the output data 714 in a grid format using specific rendering information provided, for example, by an end user. In some cases, the grid display tool 712 can also be expected to share data with other display components thereby providing not only textual and numeric image data output but rendering of an image(s) associated with the accessed data.

It should be noted at this point of the discussion that the application 700 can be saved to a workspace file located in the persistent memory 108 creating, in effect, an end user application having prepackaged functionality. Since the data tools are not compiled but rather dynamically loaded by assigning a tool application to a particular folder, for example, an end user can utilize the tool application without requiring resource intensive compilation. In this way, the inventive framework architecture lends itself to independently developed tool applications that can be readily deployed as self contained files.

Figure 8:
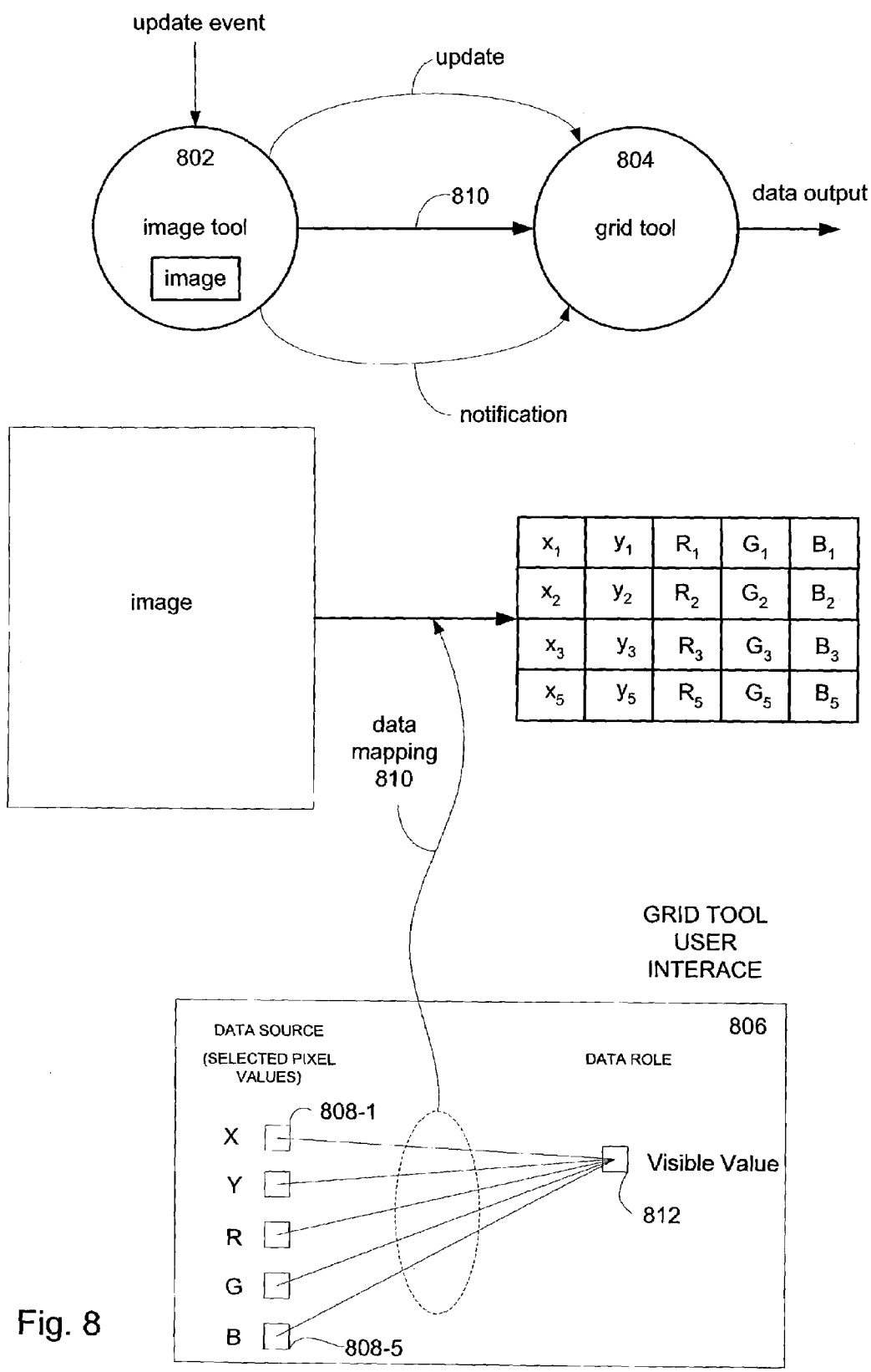
FIG. 8 shows an exemplary representative example of an image analysis application in accordance with an embodiment of the invention.

FIG. 8 shows a representative user interface 800 suitable for configuring an image analysis application 801 similar to the application 700 described above. Accordingly, the application 801 includes an image tool 802 acting as the data producer and a grid tool 804 acting as the data consumer. As configured, the grid tool 804 accesses data from the image tool 802 in the form of (x,y) coordinates of a selected group of pixels and the associated RGB color values for each pixel. In the described embodiment, the image analysis application 801 has rendered a user interface 806 that includes various user input icons 808 suitable for dynamically interfacing with an end user. As shown, the user interface 806 includes input icons 808-1 through 808-5 corresponding to the selectable portion of the data source which in this case are, respectively, the x coordinate, the y coordinate, and the various RGB values, RED, GREEN, and BLUE values.

In order for the grid tool 804 to properly process the data provided by the image tool 802, a data tool creator defines the relationship between the grid tool 804 and the image tool 802 by defining a data mapping context 810 using the various input icons 808 associated with the data source (associated with the image tool 802) and an input icon 812 ("visible value") associated with the grid tool 804. One technique for defining the mapping context 810 is shown in FIG. 8 whereby the end user manually links a desired one (or set of) input icons 808 associated with the image tool 802 and the appropriate input icon 812 (in this case the only input icon) associated with the grid tool 804. For example, if the end user wishes to view the (x,y) coordinate data for a selected pixel (or pixels), the end user would manually link the X icon 808-1 and the Y icon 808-2 to the visible value icon 812. Once set, the end user can then select those of the RGB color values to display by the grid tool 804. For example, the end user can select to display all RGB color values by linking the RGB color icons 808-3 through 808-5, respectively, to the visible value icon 812.

The image analysis application 800 is then available for analyzing (which in the case of the grid tool is rendering a grid table suitable for listing pixel co-ordinates and associated color data) that portion of the source data (i.e., image) that is made accessible by the image tool 802 to the application. In one aspect of the invention, the grid tool 804 is dynamically linked to the image tool 802 such that when necessitated by a user input event (such as, for example, changing the image subset), the grid tool 804 is notified that the input data has, or will soon, change and to await (by stalling any pending analysis operations) an update event in order to provide the correct output data. In this way, the image analysis application 800 is capable of providing an interactive and dynamic data analysis environment well suited for performing complex data analyses on a relatively large data base.

Figure 9:
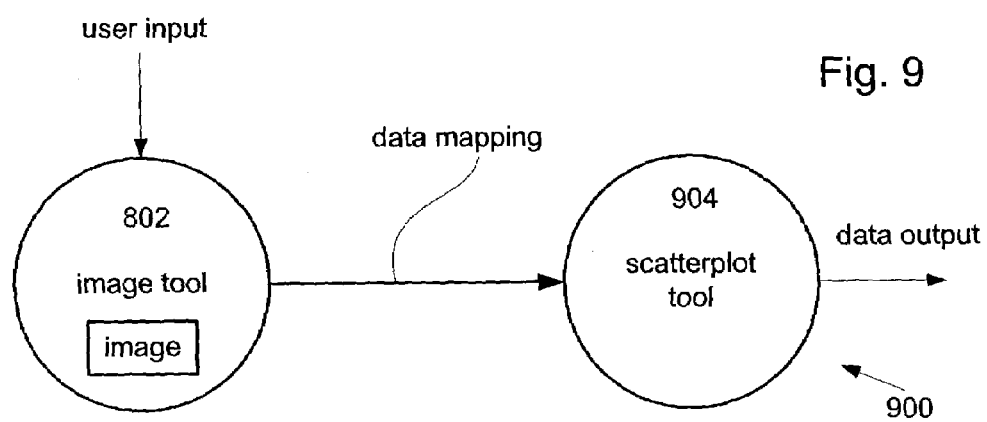
FIG. 9 illustrates an example of another tool based application in the form of a scatter plot application in accordance with an embodiment of the invention
Figure 9:
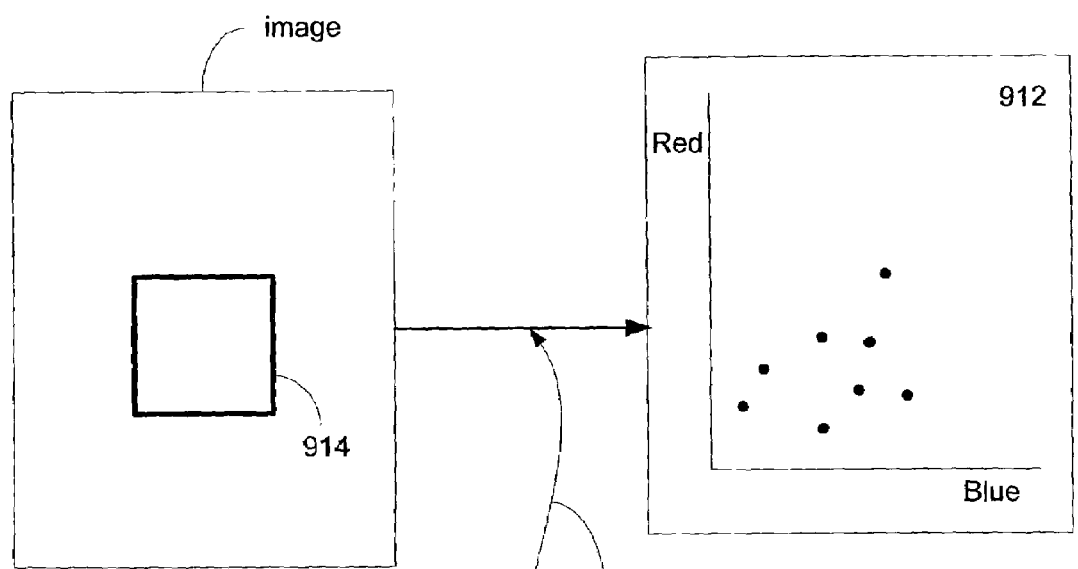

FIG. 9 illustrates an example of another tool based application in the form of a scatter plot application 900 in accordance with an embodiment of the invention. As with the example above, the image tool 802 can be linked to a scatter plot tool 904 by way of a user interface 906. The end user will then define a data mapping context 908 by manually linking selected ones of icons 909 associated with the image tool 902 to selected ones of the icons 910 associated with the scatter plot tool 904. For example, in FIG. 9, the end user has decided to display a scatter plot 912 of the Red (R) color component against the Blue (B) color component of each pixel in a data subset 914 of the image. Therefore, the user forms the appropriate mapping context by simply linking the appropriate color component icons to the appropriate output icon of the scatter plot tool 904.

As previously discussed, the end user can at any time change either the source data provided to the scatter plot tool or in some cases may even dynamically change the mapping context. For example, if the end user decided to change the subset of data viewed on the display in the form of a scatter plot, then the end user would merely select a different portion of the image to view. This can be done by any number of techniques that includes but are not limited to, a cursor based selection tool selecting a portion of the image to process or by rendering a virtual window associated with any of the data application components which can then be used to update a current state of the component by, for example, changing any of the viewed data. In some cases, the user may also wish to change the variables which are being displayed on the scatter plot by modifying the mapping context by way of the mapping context user interface. This can be easily done by simply connecting the desired input icons 910 to the output icon.

Again, as with the example above, if any source data is changed, a notification event is triggered notifying any downstream components (which in this case is the scatter plot tool 904) that a potential change in source data is impending and to suspend processing until such time as the relevant data is updated to reflect the new data (i.e., synchronization).

Figure 10:
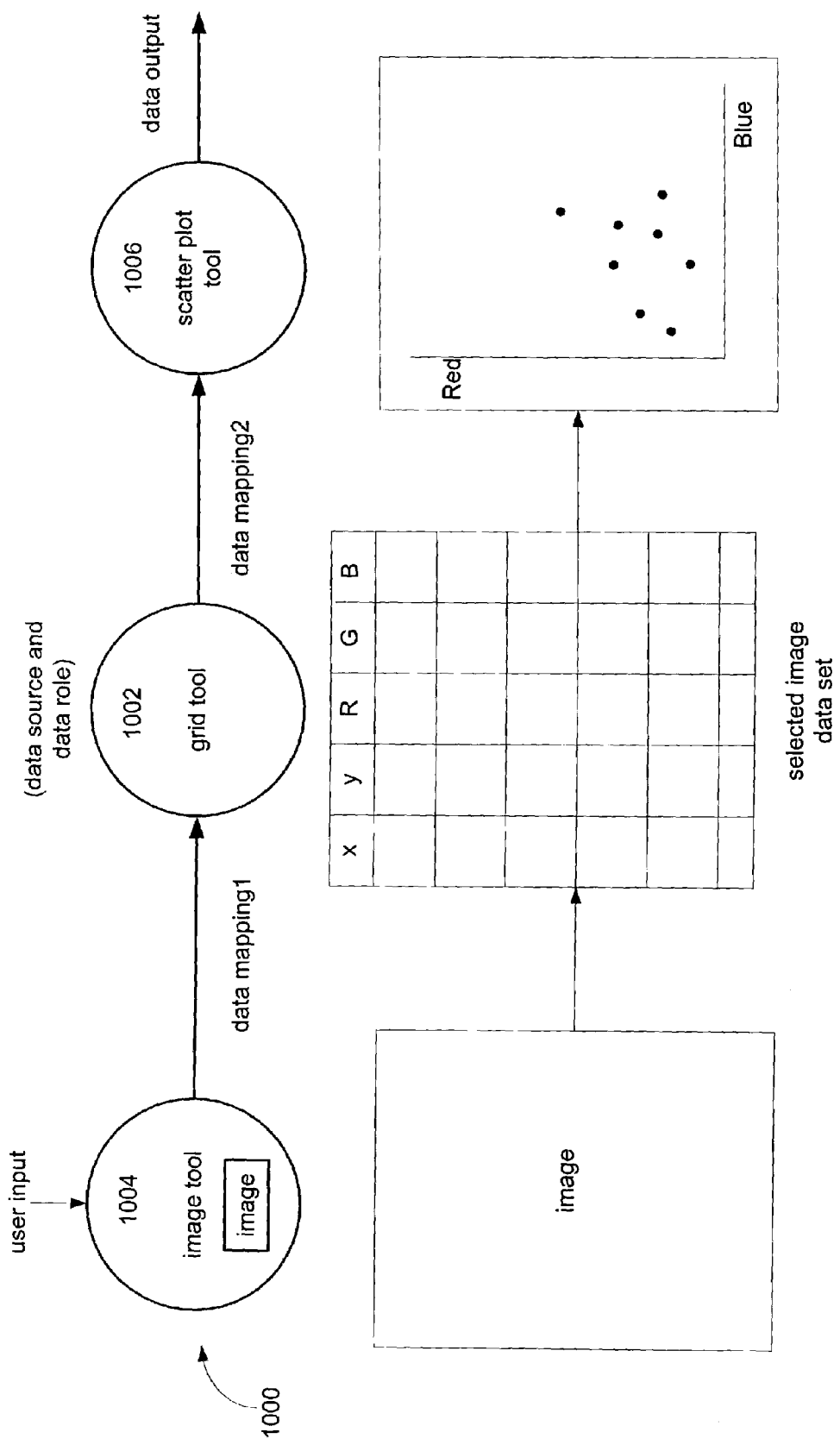
FIG. 10 shows a case whereby a data tool can be configured to act as both a data producer and a data consumer.
Figure 11:
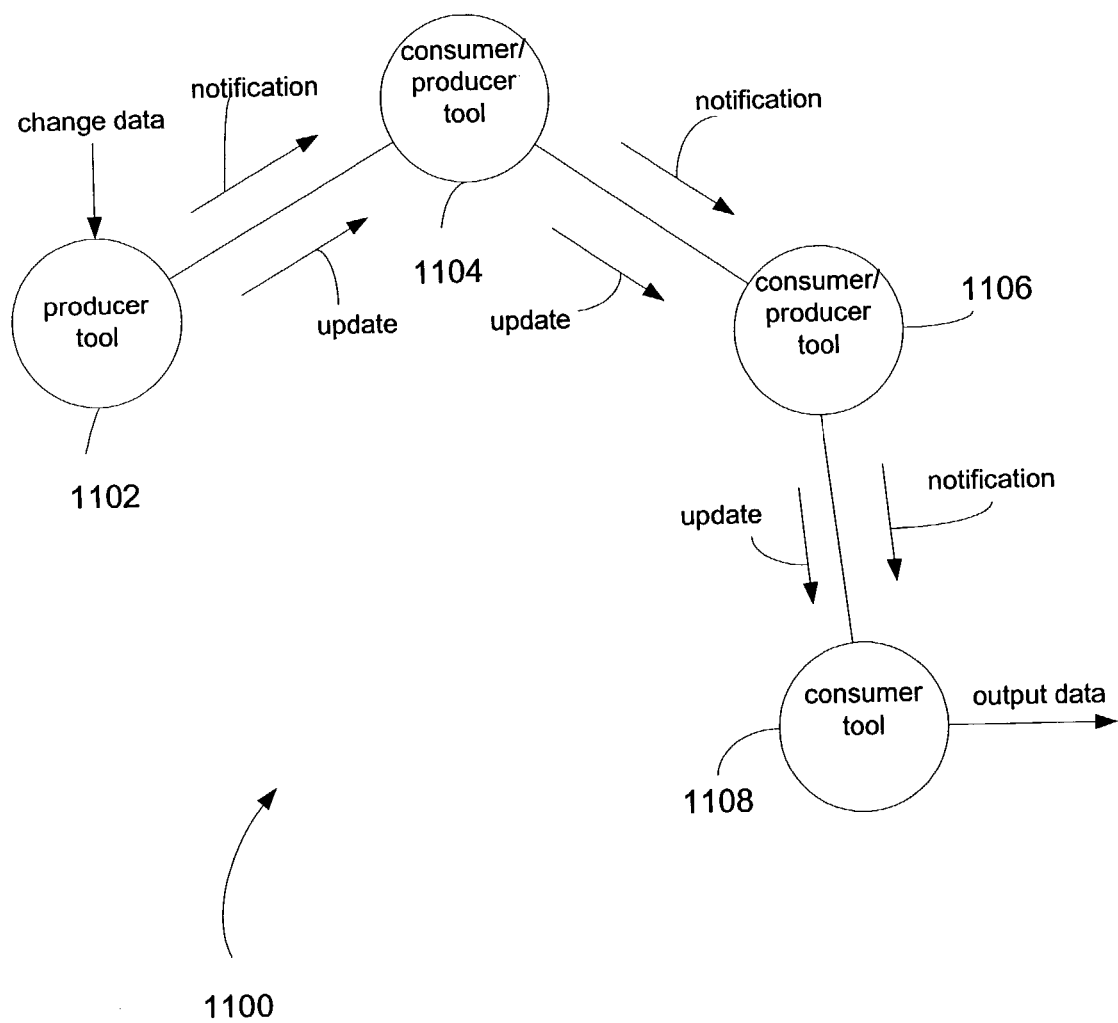
FIG. 11 shows a generalized framework in accordance with an embodiment of the invention.
Figure 12:
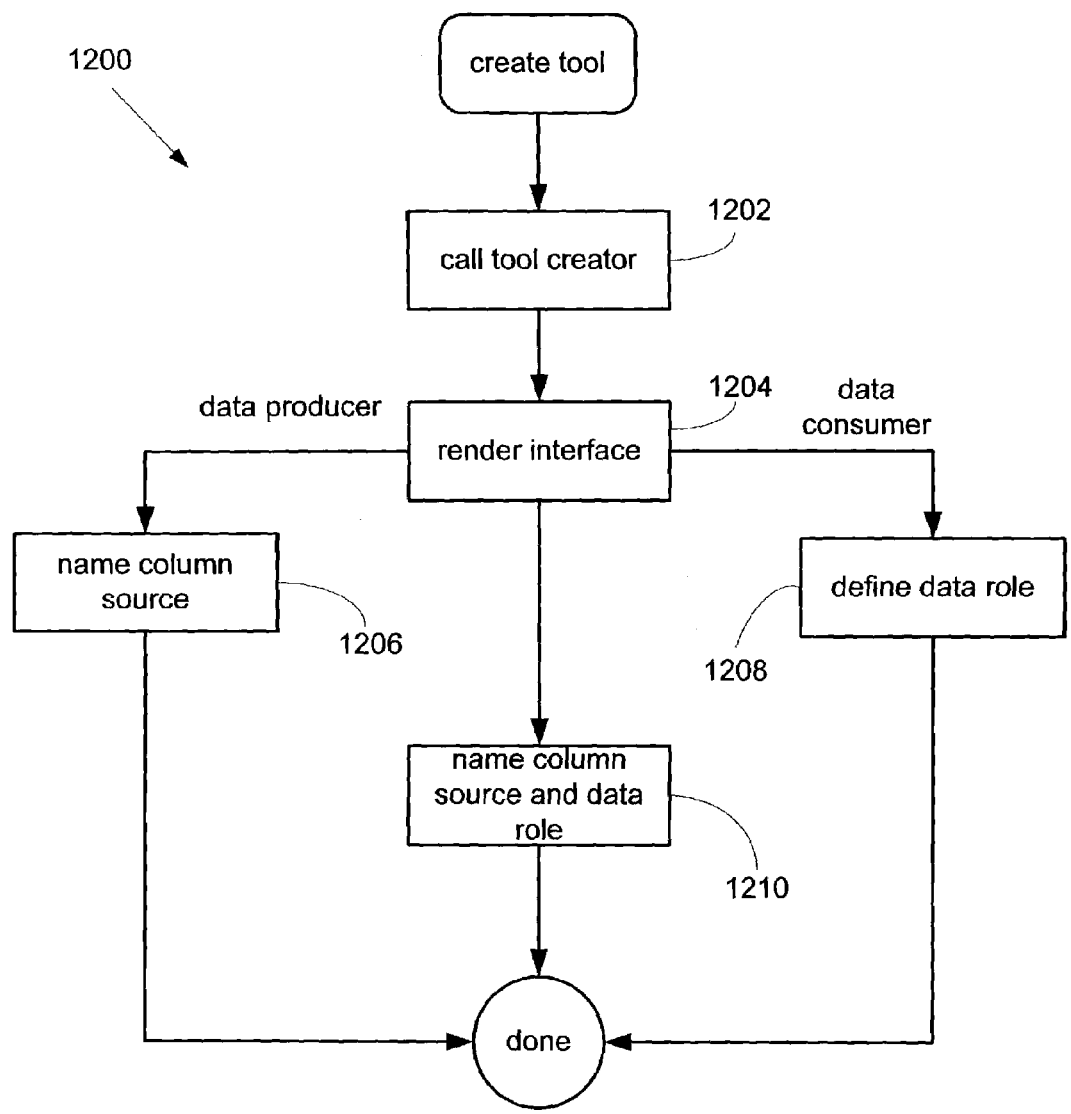
FIG. 12 shows a flowchart for creating a data tool in accordance with an embodiment of the invention.

FIG. 10 shows a case whereby a data tool can be configured to act as both a data producer and a data consumer. Accordingly, FIG. 10 shows an application 1000 that uses a grid tool 1002 as both a data consumer in relation to an image tool 1004 while acting as a data source to a scatter plot tool 1006. In this example, the image data is first provided to the grid tool 1002 that may or may not provide a display of the associated data. The grid tool 1002, in turn, acts as a data source to the scatter plot tool 1006 in order to plot and display the data provided. In this way, any changes to the data at the grid tool level is not translated back to the image tool 1004, but is however, passed forward to the scatter plot tool 904 indicating that the source data (for the scatter plot tool 1006) has changed. In the case, however, where data associated with the image tool 1004 has changed, then the notification and updating is propagated to all downstream components of the application 1000 in order to assure that any changes are reflected in the appropriate components. This updating provides a mechanism that substantially assures changes in data are appropriately and dynamically accounted for thereby maintaining the integrity of the application 1000. A more general description of the notification and updating features of the inventive framework are illustrated in FIG. 11 showing a data analysis application in the form of a generalized component based framework 1100 in accordance with an embodiment of the invention. It should be noted that the framework 1100 is a representative framework used to merely illustrate the notification and updating features. Thus, in the situation described in FIG. 11, an updating event (i.e., any event that has the capacity to change any portion of a source data set) has been invoked by, for example, a specific end-user. These updating events typically involve changing data sets, recalculating data sets, or merely including (or excluding) portions of a data set already represented. Once the updating event has been invoked, a notification signal is sent to every "downstream" component (where by "downstream" it is meant every component logically and or computationally coupled to the component which receives the update event between that component and the output node of the framework). In the example of FIG. 11, if the component 1102 is the component receiving the update event, a notification is sent to components 1104–1108 whereas if the component 1104 was the receiving component, then only components 1106–1108 receive the notification. When a component receives such a notification, by default in most cases, an update flag is set to TRUE indicating that processing by the associated component must stop until such time as that component's data is updated to reflect the new state of its source data. This process continues for all downstream components until such time as all data is updated at which time, the framework 1100 resumes operation.

The invention will now be described in terms of a number of processes described in terms of flowcharts shown in FIGS. 12–16 that can be performed by any number of mechanisms. For example in one case, the various processes can be performed as part of a object oriented computing system using an object based language such as UML. Accordingly, in order to configure a data tool, a process 1200 can be used according to the flowchart shown in FIG. 12. The process 1200 begins at 1202 by calling a tool creator that typically provides a user interface that enables a user to create a data tool. Next, at 1204, a tool creator interface is rendered on the user interface that presents a number of options for creating a particular type of data tool. In a particular embodiment, the tool creator interface provides for user input specifically related to defining a tool type (i.e., a data producer, a data consumer, or a data producer/consumer), a tool type name, as well as an option to instantiate the tool at startup. In the case where the tool type is a data producer type tool, then at 1206, the column sources associated with each data source are named. In the case where the tool type is a data consumer type tool, then at 1208 the data role for the data consumer is defined. In the case where the tool type is a data consumer/producer tool, that at 1210, both the column sources associated with each data source is named, and the data role for the data consumer is defined. It should be noted, that the various data tools can be pre-defined and stored in a workspace included in, for example, the persistent store 108 of FIG. 1 and made available as part of a library of data tools. In this way, a user merely selects particular data tools based upon the requirements of the data analysis to be performed thereby avoiding the necessity to redefine the various data tools for every application created.

Figure 13:
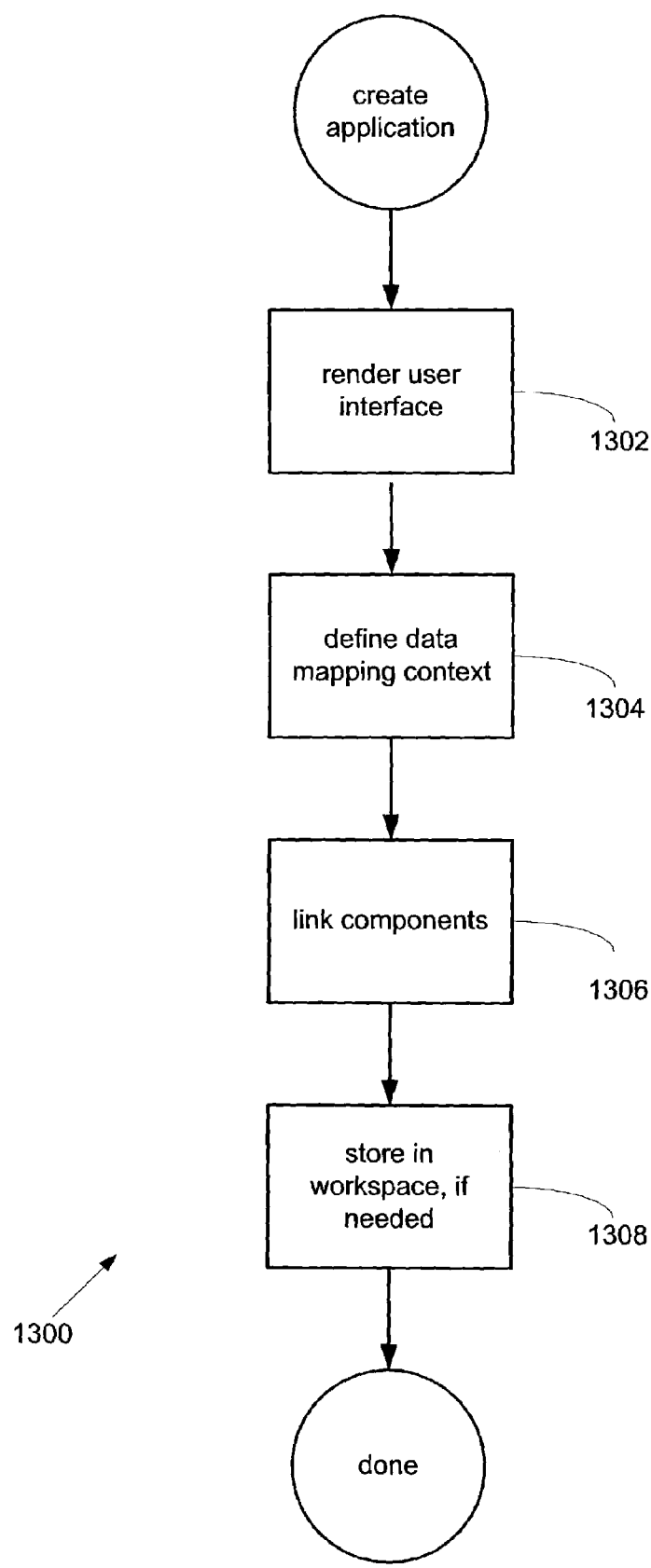
FIG. 13 shows a flowchart detailing a process for creating an application in accordance with an embodiment of the invention.

Once the various data tools have been obtained (either by original creation or retrieval from a pool of stored data tools), an application is created using the aforementioned tools according to a process 1300 shown as a flowchart in FIG. 13. Accordingly, at 1302, each data tool renders an associated user interface in such as way to enable a user to define a mapping context between a data producer and a data consumer tool at 1304. Once the mapping context has been instantiated, a framework builder links the various framework components by way of the associated mapping contexts at 1306 thereby creating a framework suitably disposed to provide appropriate data analysis engine in the form of a workspace application, if so desired, by storing the framework in a workspace file at 1308. The application can then be deployed to any number of end users by merely opening the workspace file and invoking the application stored therein using any number and type of input commands.

An example of a useful workspace file is described below with regards to genotyping a diploid sample. As well known in the arts, a diploid is a full set of genetic material formed of paired chromosomes, one chromosome from each parent typical of most animal cells (the diploid human genome, for example, has 46 chromosomes). Analysis of such data is useful since in diploid organisms, such as humans, the linkage of particular SNP genotypes on each chromosome in a homologous pair (the haplotype) may provide additional information that is not available from SNP genotyping alone. This information is useful since SNP genotype data may be used to map disease loci through linkage disequilibria or association studies providing diagnostic markers for human disease As background to the following discussion, note is taken of the Hardy Weinberg Equilibrium relation ($P^2+2PQ+Q^2=1$) that predicts frequencies of alleles in the next generation (when combined at random) given the current allele frequencies (where P and Q are frequencies of the two alleles). In those situations where sampling an entire population is unrealistic, well known statistical techniques provides the ability to make an estimate, based upon a sample of the population rather than using the entire population. For example, when every individual in a population can not be sampled, the term P-hat is used to estimate P. If the sampling and estimation of P were repeated many times using the same population, then the values of Phat are expected to cluster symmetrically around P according to the standard error (i.e., ~68% of estimates of Phat are within + or −1 S.E. of p).

Figure 14:
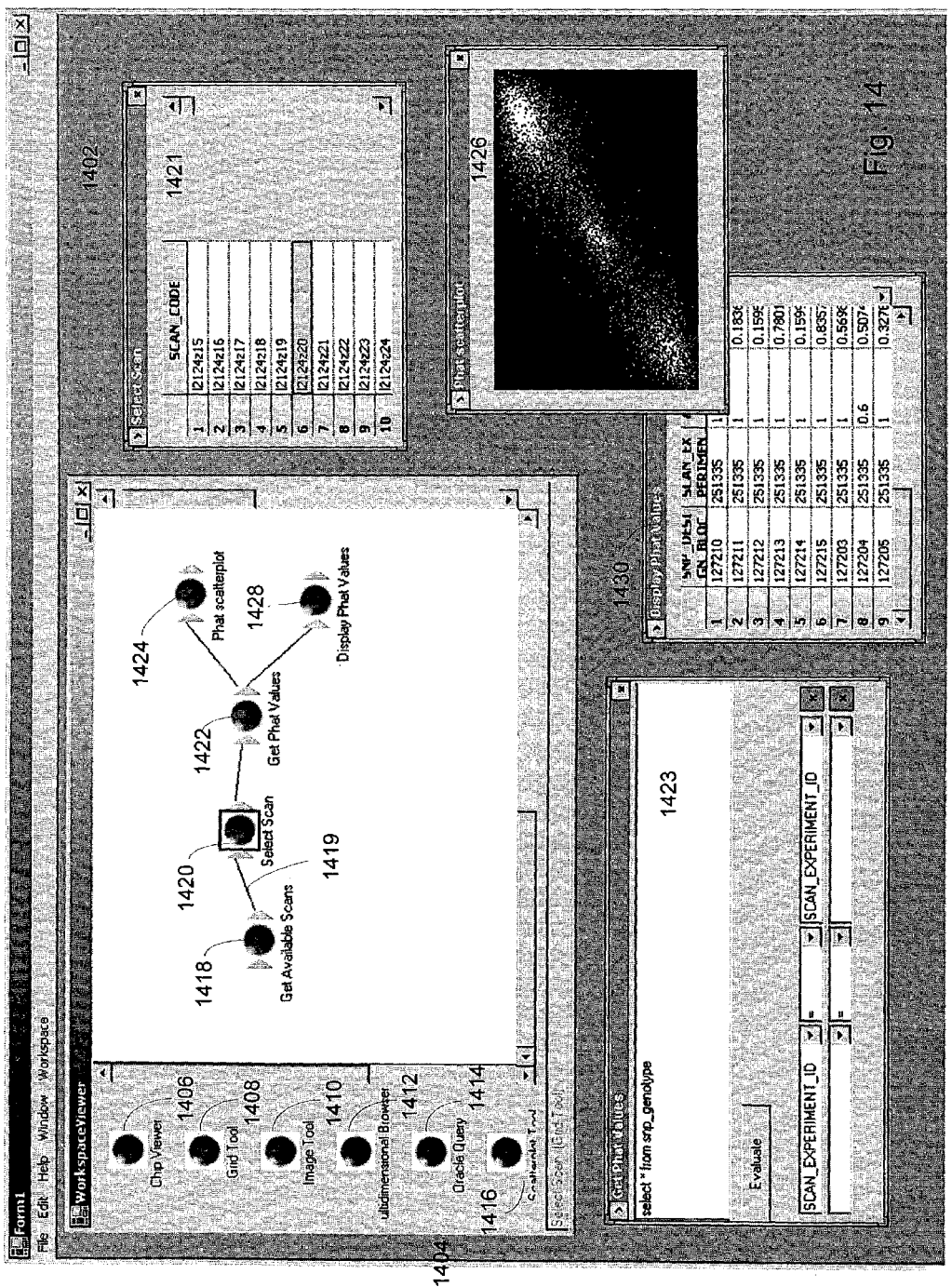
FIG. 14 shows a representative tool base application in accordance with an embodiment of the invention.
Figure 15:
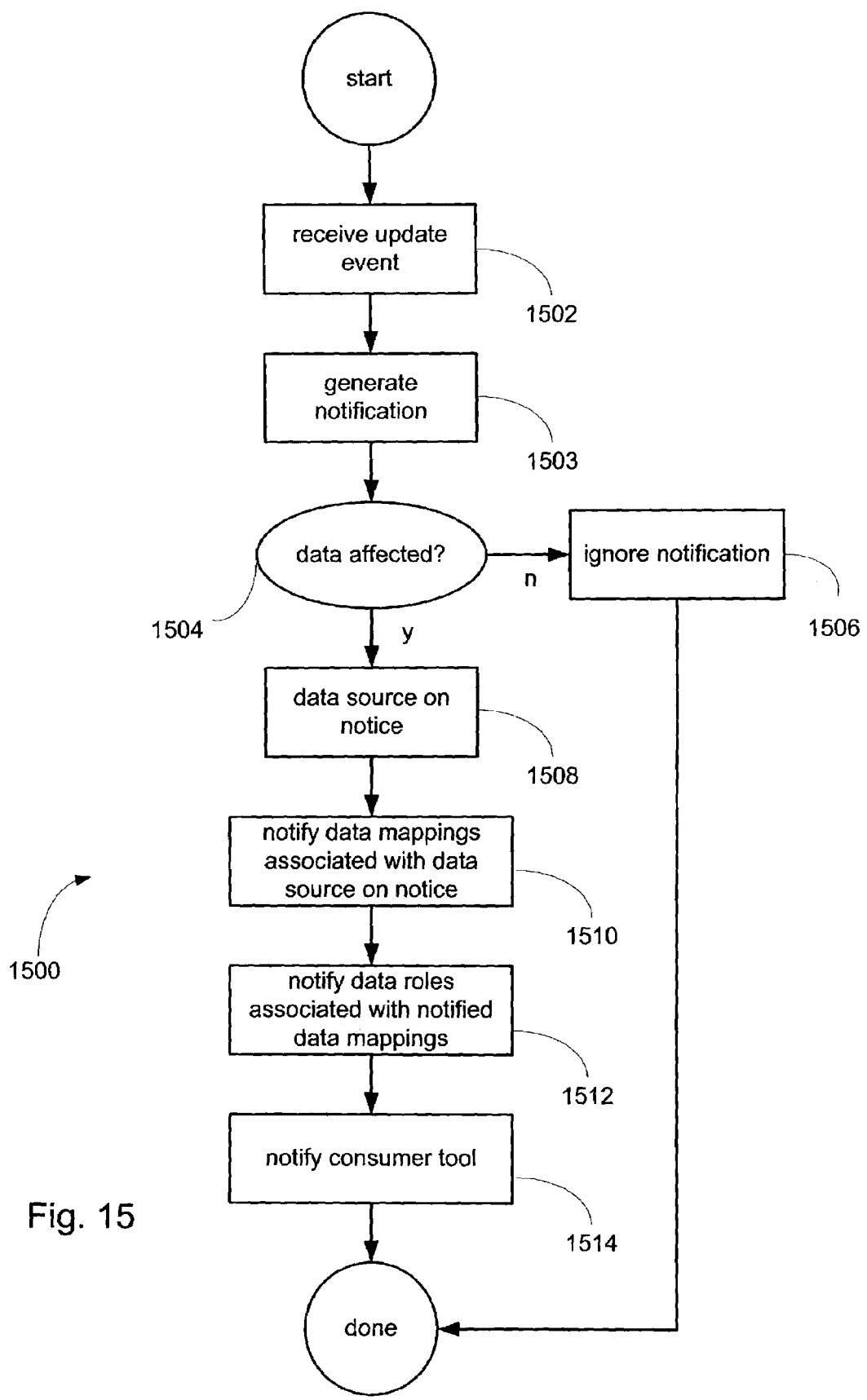
FIG. 15 shows a flowchart detailing a notification process in accordance with an embodiment of the invention.

Accordingly, FIG. 14 illustrates an example of an application 1400 configured to provide user interactive data analysis tool for analyzing data from the genotyping of a diploid sample in which every SNP location in the sample has a value of P of 0.5 or 1.0. In the described embodiment, the genotyping analysis application 1400 is formed of a number of components each of which is shown as part of a workspace 1402. Of particular note is the library of available tools 1404 showing a list of available pre-defined data tools ready for use. For example, the list of pre-defined data tools includes a chip viewer tool 1406, a grid tool 1408, an image tool 1410, a multidimensional browser tool 1412, an oracle query tool 1414, and a scatter plot tool 1416 to name but a few. In addition, other tools include a sequence annotation browser tool useful for annotating genomic data. As shown in FIG. 14, the application 1400 is formed of a number of components in the form of data tools, at least one being a data source tool (i.e., "Get Available Scans" tool 1418) that represents source data from available scans stored in a genomic data base. Using a user supplied mapping context 1419, a grid tool configured as a select scan tool 1420 operates to select certain of the data provided by the "Get Available Scans" tool 1418. In the described embodiment, a current state of a tool can be "viewed" through a selectable window. For example, just such a window, in the form of an interface 1421 rendered by the "Select Scan" tool 1420, shows a number of available scans (in the form of scan codes) each of which can be readily selected by a user. As discussed previously, a grid tool consumes data in the form of a single table and provides only selected rows of data, which in the case of the select scan tool 1420 are Phat values associated with a selected scan. In the particular case shown, the selected Phat values are associated with a selected scan having a scan code "2123z20" as source data for a "Get Phat Values" tool 1422. The Get Phat Values tool 1422, in turn, provides a user the ability to select a particular subset of the Phat values provided thereof (which in this case is derived from "SNP_genotype"). Once the data has been selected, a "Phat Scatter plot" tool 1424 generates and renders a Phat scatter plot 1426 configured for displaying the forward vs. reverse strand Phat values calculation for each SNP for that scan. Concurrently a "Display Phat Values" tool 1428 renders a corresponding "Display Phat Values" display 1430.

It should be noted that as different scan codes are selected, the observed scatter plot will auto update to reflect change in input data illustrating the capability of providing real time updating. When different tools use the same source data then what is referred to as a highlighted shared selection state provides for concurrent updating of displayed data. For example, updating of any of the source data (such as the Phat values) results in a concurrent updating of the various displayed output data (i.e., the Phat scatter plot display 1426 and/or the Display Phat Values display 1430).

Whenever data is changed, downstream components must be notified in order to assure data integrity throughout the network. Accordingly, a notification process 1500 arranged to notify all components of a change in a state of a data source is described in terms of a flowchart shown in FIG. 15. The process 1500 begins at 1502 by a data source component receiving an update event that has the potential to change the data provided. Such an update event includes user initiated data change requests that could include, for example, selecting different portions of a data base, changing data bases entirely, or modifying selected subsets of a previously selected portion of a data base. Once a notification event is received by the data source at 1502, a determination is made at 1504 whether or not the data provided by the data source is affected. If it is determined that the data provided by the data source is not affected by the notification event, then the notification event is ignored, otherwise, at 1506, each data source associated with a data producer is notified that its particular data is subject to being updated. Next, at 1508, each data mapping associated with the notified data sources are, in turn notified, whereas at 1510, each data role associated with the notified data mappings are subsequently notified as well. It should be noted at this point, that in the described embodiment, an update flat is by default set to TRUE thereby stalling any operations that an associated data tool is performing until such time as the update flag is set to FALSE. In some cases, however, a particular data tool may not by default set its update flag to TRUE upon receiving a notification.

Once the appropriate data roles have been notified, the appropriate consumer tool is notified at 1512. If the notified consumer tool is in fact a producer tool to any downstream components, then the notified consumer tool provides a notification event (i.e., acts as a producer) to the necessary downstream components at 1502 and the process repeats until there are no additional components to notify. In this way, the notification event ripples downstream to all components that are linked to the data source that originally received the update event.

Figure 16:
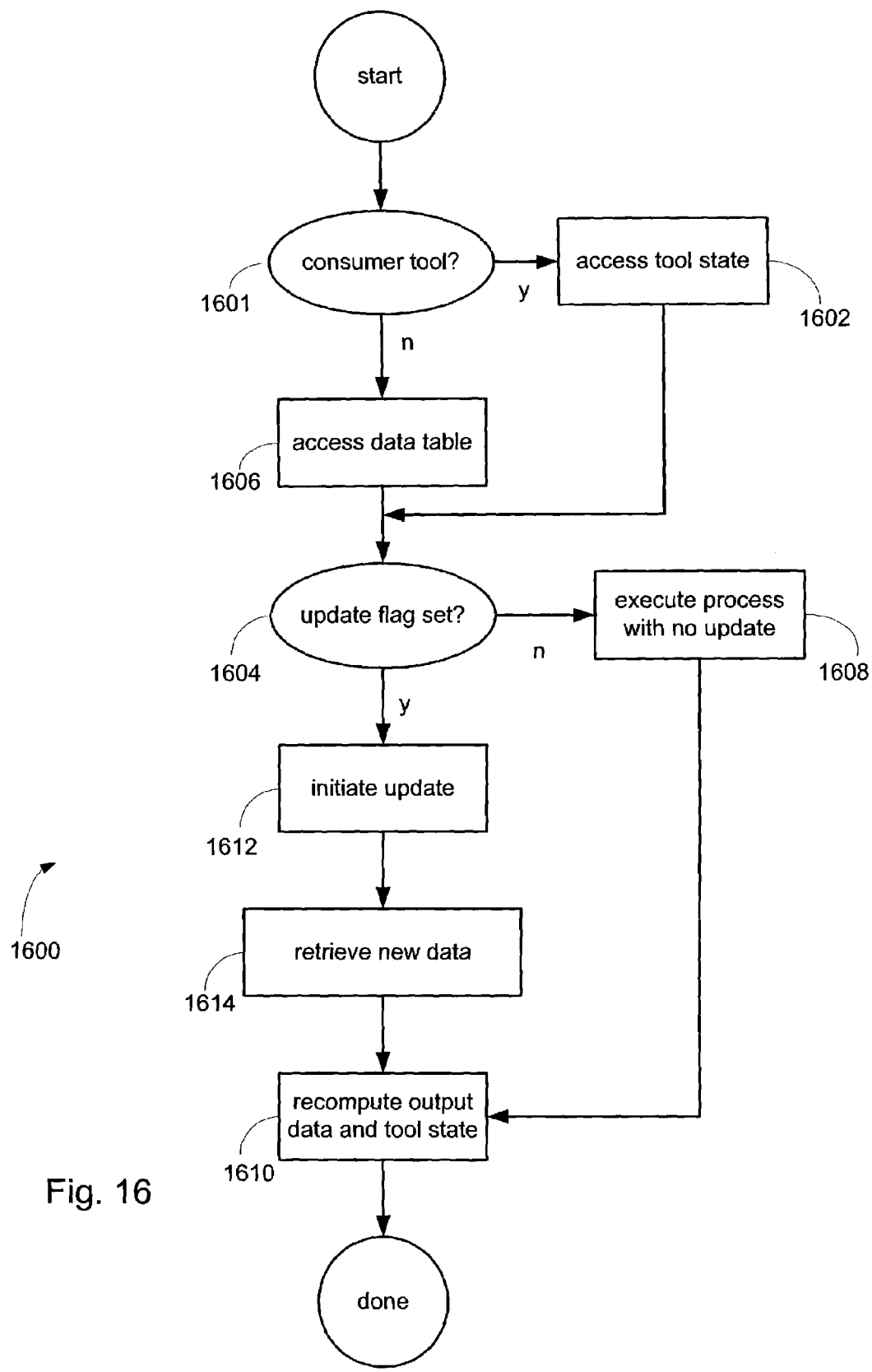
FIG. 16 shows a flowchart detailing an update process in accordance with an embodiment of the invention.

Once all the appropriate components have been notified and are prepared to be updated (i.e., update flag is set), then an update process 1600 is initiated as described in a flowchart shown in FIG. 16. Accordingly, at 1601, if the tool is a consumer tool, then the tool state is accessed at 1602 and control is passed to 1604 where a determination is made whether or not the update flag is set to TRUE. On the other hand, if the data tool is a producer type tool, then a data table associated with the data source is obtained at 1606 and control is passed to 1604 for a determination of the status of the update flag. If at 1604, the update flag is determined to set to FALSE, then the process request is executed at 1608 and both internal state and output data is recomputed at 1610. On the other hand, if the update flag is determined to be set to TRUE, then at 1612, the data tool performs the update operation by obtaining the appropriate input data from the data producer at 1614 after which the internal state and output data is recomputed at 1610. The procedure continues for all components in the network after which the update process is complete and the process 1600 ends.

Figure 17:
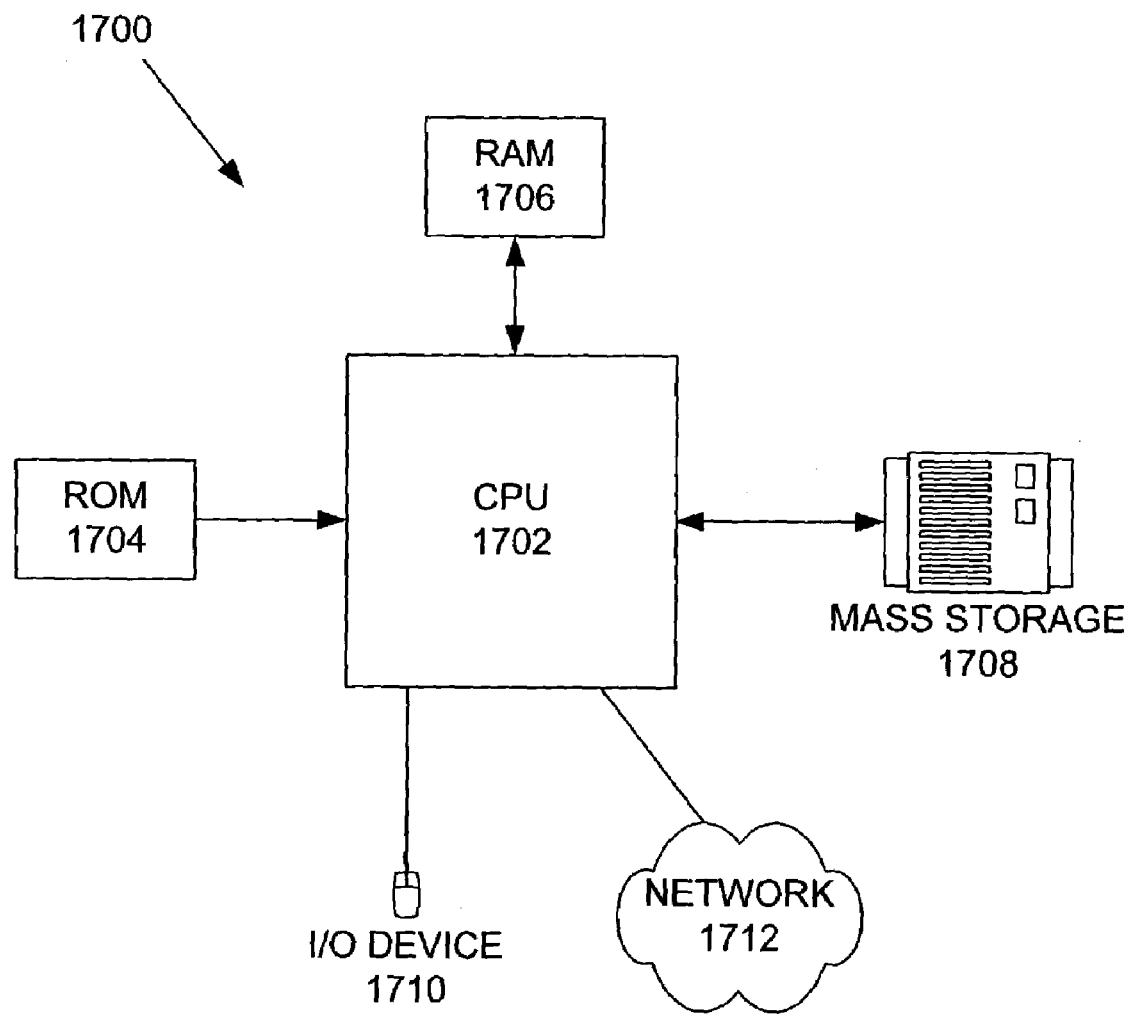
FIG. 17 illustrates a typical, general-purpose computer system suitable for implementing the present invention.

FIG. 17 illustrates a typical, general-purpose computer system suitable for implementing the present invention. Computer system 1700 or, more specifically, CPUs 1702, may be arranged to support a virtual machine, as will be appreciated by those skilled in the art. As is well known in the art, ROM acts to transfer data and instructions unidirectionally to the CPUs 1702, while RAM is used typically to transfer data and instructions in a bi-directional manner. CPUs 1702 may generally include any number of processors. Both primary storage devices 1704, 1706 may include any suitable computer-readable media. A secondary storage medium 1708, which is typically a mass memory device, is also coupled bi-directionally to CPUs 1702 and provides additional data storage capacity. The mass memory device 1708 is a computer-readable medium that may be used to store programs including computer code, data, and the like. Typically, mass memory device 1708 is a storage medium such as a hard disk or a tape which generally slower than primary storage devices 1704, 1706. Mass memory storage device 1708 may take the form of a magnetic or paper tape reader or some other well-known device. It will be appreciated that the information retained within the mass memory device 1708, may, in appropriate cases, be incorporated in standard fashion as part of RAM 1706 as virtual memory. A specific primary storage device 1704 such as a CD-ROM may also pass data uni-directionally to the CPUs 1702.

CPUs 1702 are also coupled to one or more input/output devices 1010 that may include, but are not limited to, devices such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPUs 1702 optionally may be coupled to a computer or telecommunications network, e.g., an Internet network or an intranet network, using a network connection as shown generally at 1012. With such a network connection, it is contemplated that the CPUs 1702 might receive information from the network, or might output information to the network in the course of performing the above-described method steps. Such information, which is often represented as a sequence of instructions to be executed using CPUs 1702, may be received from and outputted to the network, for example, in the form of a computer data signal embodied in a carrier wave. The above-described devices and materials will be familiar to those of skill in the computer hardware and software arts.

Although only a few embodiments of the present invention have been described, it should be understood that the present invention might be embodied in many other specific forms without departing from the spirit or the scope of the present invention. The present examples are to be considered as illustrative and not restrictive, and the invention is not to be limited to the details given herein, but may be modified within the scope of the appended claims along with their full scope of equivalents.

The invention claimed is:

1. In an object oriented computing environment, a method of configuring an interactive data analysis application arranged to perform real time data analysis of selected data from a complex data base, comprising:

instantiating a configurable data tool object wherein the data tool object is configurable as a selected analysis application component;

configuring the data tool object as a data producer for providing access to the selected data;

configuring the data tool object as a data consumer for providing the analysis of the selected data, mapping the data producer to the data consumer by way of a mapping context; and concurrently updating and analyzing the selected data.

2. A method as recited in claim 1, further comprising:

rendering a virtual window;

associating the virtual window with a selected one of the data analysis application components; and viewing a current state of the associated data analysis application components.

3. A method as recited in claim 2, further comprising:

updating the current state by providing an update event by way of the virtual window.

4. A method as recited in claim 3, further comprising:

in response to the update event, generating a notification event by the updated data analysis application component; and sending the notification event to those data analysis application components that are downstream of the updated data analysis application component.

5. A method as recited in claim 4, further comprising:

for each downstream data analysis application component in response to the notification event, querying an update flag status stalling data analysis operations based upon the queried update flag status;

receiving updated data consistent with the updated state; and analyzing the updated data.

6. A method as recited in claim 1, further comprising:

deploying the application to a selected workspace file; and executing the deployed application without compilation.

7. A method as recited in claim 1, fiber comprising:

configuring the data toot as a data producer/consumer arranged to, access the selected data, perform the data analysis, and output the analyzed data to the data consumer.

8. In an object oriented computing environment, computer program product for configuring an interactive data analysis application arranged to perform real time data analysis of selected data from a complex data base, comprising:

computer code for instantiating a configurable data tool object;

computer code for configuring the data tool object as a data producer for providing access to the selected data;

computer code for configuring the data tool object as a data consumer for providing the data analysis of the selected data, computer code for concurrently undating an analyzing the selected data; and computer readable medium for storing the computer code.

9. Computer program product as recited in claim 8, further comprising:

computer code for rendering a virtual window;

computer code for associating the virtual window wit a selected one of the data analysis application components; and computer code for viewing a current state of the associated data analysis application components.

10. Computer program product as recited in claim 9, further comprising:

computer code for updating the current state by providing an update event by way of the virtual window.

11. Computer program product as recited in claim 10, further comprising:
   computer code for generating a notification event by the updated data analysis application component in the response to the updating event; and
   computer code for sending the notification event to those data analysis application components that are downstream of the updated data analysis application component.

12. Computer program product as recited in claim 11, further comprising:
   for each downstream data analysis application component in response to the notification event,
   computer code for querying an update, flag status
   computer code for stalling data analysis operations based upon the queried update flag status;
   computer code for receiving updated data consistent with the updated state; and
   computer code for analyzing the updated data.

13. Computer program product as recited in claim 8, further comprising:
   computer code for deploying the application to a selected workspace file; and
   computer code for executing the deployed application without compilation.

14. Computer program product as recited in claim 8, further comprising:
   computer code for configuring the data tool as a data producer/consume arranged to,
   computer code for access the selected data,
   computer code for perform the data analysis, and
   computer code for output the analyzed data to the data consumer.

15. In an object oriented computing environment, an interactive data analysis application arranged to perform real time data analysis of selected data from a complex data base, comprising:
   a configurable data tool object configured as,
      a data producer for providing access to the selected data, and
      a data consumer for providing the data analysis of the selected data;
   a mapping context that associates the data producer to the data consumer to form the interactive data analysis application wherein the configurable data tool object concurrently updates and analyzes the selected data.

16. An application as recited in claim 15, wherein the configurable data tool is
   configured as a data producer/consumer arranged to access the selected data,
   perform the data analysis, and output the analyzed data to the data consumer.

17. An application as recited in claim 15 further comprising:
   a virtual window renderer for creating a virtual window, wherein the virtual window is associated with at least a selected one of the data analysis application components such that a current state of the associated data analysis application component is ascertainable by way of the window.

18. An application as recited in claim 17, wherein the current state is updated by providing an update event by way of the virtual window.

19. An application as recited in claim 18, further comprising:
   a notification event generator for generating a notification event in response to the update event by the updated data analysis application component which is sent to those data analysis application components that are downstream of the updated data analysis application component.

* * * * *